(12) United States Patent
Yager (10) Patent No.: US 6,277,641 B1
(45) Date of Patent: Aug. 21, 2001

(54) METHODS FOR ANALYZING THE PRESENCE AND CONCENTRATION OF MULTIPLE ANALYTES USING A DIFFUSION-BASED CHEMICAL SENSOR

(75) Inventor: Paul Yager, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/441,572

(22) Filed: Nov. 17, 1999

Related U.S. Application Data (62) Division of application No. 08/938,093, filed on Sep. 26, 1997, now Pat. No. 6,007,775.

(51) Int. Cl.[7] .................................................. G01N 35/08
(52) U.S. Cl. ............................ 436/52; 436/53; 436/172; 436/177; 436/180
(58) Field of Search ................................ 436/52, 53, 172, 436/177, 180; 422/81, 82, 82.01, 82.08, 82.05

(56) References Cited

U.S. PATENT DOCUMENTS

| | | | |
|---|---|---|---|
| 3,795,489 | 3/1974 | Warnick et al. | 23/254 R |
| 4,486,097 * | 12/1984 | Riley | 356/410 |
| 4,894,146 | 1/1990 | Giddings | 209/12 |
| 4,983,038 | 1/1991 | Ohki et al. | 356/246 |
| 5,007,732 | 4/1991 | Ohki et al. | 356/73 |
| 5,019,515 | 5/1991 | Gisin et al. | 436/52 |
| 5,039,426 | 8/1991 | Giddings | 210/695 |
| 5,240,618 | 8/1993 | Caldwell et al. | 210/748 |
| 5,250,263 | 10/1993 | Manz | 422/81 |
| 5,304,487 | 4/1994 | Wilding et al. | 435/29 |
| 5,585,069 | 12/1996 | Zanzucchi et al. | 422/100 |
| 5,635,358 | 6/1997 | Wilding et al. | 435/7.2 |
| 5,707,799 | 1/1998 | Hansmann et al. | 435/6 |
| 5,716,852 * | 2/1998 | Yager et al. | 436/172 |
| 5,773,298 * | 6/1998 | Lynggaard et al. | 436/52 |
| 5,932,100 * | 8/1999 | Yager et al. | 210/634 |
| 5,948,684 * | 9/1999 | Weigl et al. | 436/52 |
| 5,972,710 * | 10/1999 | Weigl et al. | 436/34 |

FOREIGN PATENT DOCUMENTS

| | | |
|---|---|---|
| 0 294 701 B1 | 9/1992 | (EP) . |
| WO 96/12541 | 5/1996 | (WO) . |
| WO 96/15576 | 5/1996 | (WO) . |
| WO 97/00125 | 1/1997 | (WO) . |
| WO 97/00442 | 1/1997 | (WO) . |

OTHER PUBLICATIONS

Chmelik, J., "Isoelectric focusing field–flow fractionation experimental study of the generation of pH gradienta"(Feb. 8, 1991)*J. Chromatography* 539(1):111–121.

* cited by examiner

*Primary Examiner*—Jeffrey Snay
(74) *Attorney, Agent, or Firm*—Greenlee, Winner and Sullivan, P.C.

(57) ABSTRACT

The present invention provides a microfabricated sensor and a method capable of rapid simultaneous measurement of multiple analytes in a fluid sample. The sensor is inexpensive, disposable and portable, and requires only microliters of sample, a particular advantage with precious fluids such as blood. The sensor utilizes diffusion between layered laminar streams rather than side by side streams. This allows multiple side by side channels for simultaneous detection of multiple analytes. In the sensor, a sample stream and a carrier stream flow in layers, one on top of the other, and one or more reagents are introduced to the bottom of the carrier stream through either a fluid or a solid reagent inlet. The reagent contains reagent particles which, in the presence of the analyte, have a detectable change in a property. The analyte diffuses into the carrier stream where it interacts with reagent particles and is detected by optical, electrochemical or other devices.

26 Claims, 4 Drawing Sheets

METHODS FOR ANALYZING THE PRESENCE AND CONCENTRATION OF MULTIPLE ANALYTES USING A DIFFUSION-BASED CHEMICAL SENSOR

CROSS-REFERENCE TO RELATED APPLICATIONS

This application is a divisional of application Ser. No. 08/938,093 filed Sep. 26, 1997, now U.S. Pat. No. 6,007,775.

FIELD OF THE INVENTION

This invention relates to diffusion based microsensors and methods for analyzing the presence and concentration of multiple analytes in samples containing both these analytes and, optionally, larger particles. The invention is particularly useful for analyzing complex samples, such as blood, to detect the presence of small particles, such as ions or proteins, in a stream containing larger particles, such as cells.

BACKGROUND OF THE INVENTION

The greater diffusion of small particles relative to larger particles can be used to partially separate the species. Diffusion is a process which can easily be neglected at large scales, but rapidly becomes important at the microscale. Due to extremely small inertial forces in such structures, practically all flow in microstructures is laminar. This allows the movement of different layers of fluid and particles next to each other in a channel without any mixing other than diffusion. Moreover, due to the small lateral distances in such channels, diffusion is a powerful tool to separate molecules and small particles according to their diffusion coefficients.

Using tools developed by the semiconductor industry to miniaturize electronics, it is possible to fabricate intricate fluid systems with channel sizes as small as a micron. These devices can be mass-produced inexpensively and are expected to soon be in widespread use for simple analytical tests.

A process called "field-flow fractionation" (FFF) has been used to separate and analyze components of a single input stream in a system not made on the microscale, but having channels small enough to produce laminar flow. Various fields, including concentration gradients, are used to produce a force perpendicular to the direction of flow to cause separation of particles in the input stream (see, e.g. Giddings, J. C., U.S. Pat. No. 4,147,621; Caldwell, K. D. et al., U.S. Pat. No. 5,240,618; Wada, Y., et al., U.S. Pat. No. 5,465,849). None of these references disclose the use of a separate input stream to receive particles diffused from a particle-containing input stream.

A related method for particle fractionation is the "Split Flow Thin Cell" (SPLITT) process (see, e.g., Williams, P. S., et al. (1992), Ind. Eng. Chew. Res. 31:2172–2181; and J. C. Giddings U.S. Pat. No. 5,039,426). These publications disclose channel cells with channels small enough to produce laminar flow, but again only provide for one inlet stream. A further U.S. patent to J. C. Giddings, U.S. Pat. No. 4,737,268, discloses a SPLITT flow cell having two inlet streams. Giddings U.S. Pat. 4,894,146 also discloses a SPLITT flow cell having two input streams. All these SPLITT flow methods require the presence of more than one output stream for separating various particle fractions.

None of the foregoing publications describe a channel system capable of analyzing small particles in very small quantities of sample containing larger particles, particularly larger particles capable of affecting the indicator used for the analysis. No devices or methods provide simultaneous measurement of more than one analyte.

SUMMARY OF THE INVENTION

The present invention provides a microfabricated sensor capable of rapid simultaneous measurement of multiple analytes in a fluid sample. Reagents can be loaded into the sensor during fabrication and only the sample fluid needs to be introduced for measurement, making it ideal for use outside of the laboratory. The detection apparatus can be as simple as a human eye, a camera, or a voltmeter, which also supports field use. The sensor is sufficiently simple and inexpensive to manufacture that it is practical for disposable use. Multiple analytes can be simultaneously detected with only microliters of sample, a particular advantage with precious fluids such as blood.

The inventor previously provided a channel cell system for detecting the presence of analyte particles in a sample stream also comprising larger particles (U.S. patent applications Ser. No. 08/829,679, filed Mar. 31, 1997, now U.S. Pat No. 5,972,710, and 08/625,808, filed Mar. 29, 1996, now U.S. Pat. No. 5,716,852, both of which are incorporated by reference herein in their entirety). The previous system comprised a laminar flow channel having at least two inlets for conducting fluids into the laminar flow channel. The inlets contained (1) a sample stream containing analyte particles and also containing larger particles and (2) an indicator stream having a substance which indicates the presence of the analyte particles by a detectable change in property. The two streams flow side by side in the channel without turbulent mixing. The analyte particles diffuse into the indicator stream to the substantial exclusion of the larger particles, and their presence is detected by reaction with the indicator substance.

The present invention provides an apparatus and a method which utilize diffusion between layered laminar streams rather than side by side streams. This allows multiple side by side reagent inlets for simultaneous detection of multiple analytes. Additionally, utilizing diffusional separation, the sensor can tolerate fluid samples also containing larger particles.

In this invention, a sample stream and a carrier stream flow in layers, one on top of the other, rather than side by side. A reagent is introduced to the bottom of the carrier stream through either a fluid or a solid reagent inlet. The reagent contains reagent particles which, in the presence of the analyte, have a detectable change in a property. The sample stream can contain larger particles such as cells as well as the analytes of interest. The term "particles" refers to any species, including dissolved and particulate species such as molecules, cells, suspended and dissolved particles, ions and atoms. The analyte diffuses into the carrier stream where it interacts with reagent particles and is detected by optical, electrochemical or other means.

The sample stream may also contain larger particles, which may also be sensitive to the reagent. Because these do not diffuse into the carrier stream, they do not interfere with detection of the analyte. By diffusion of the analyte but not the larger particles, cross-sensitivities of reagents to larger sample components, a common problem, can be avoided. Furthermore, the reagent can be kept in a solution in which it displays its optimal characteristics. For example, cross-sensitivities to pH or ionic strength can be suppressed by using strongly buffered carrier solutions.

A reagent inlet joins the laminar flow channel on the surface abutting the carrier stream. For multiple analyte detection, each inlet is narrower than the flow channel. For single analyte detection the inlet can be as wide as the flow channel. A fluid reagent inlet is a fluid channel. The fluid reagent forms a stream in layered laminar flow with the carrier and sample streams, but it is a relatively thin and narrow layer since the inlet is narrower than the channel and the reagent fluid volume is small relative to the sample and carrier fluids. A solid reagent inlet is a cavity in the laminar flow channel on the side containing the carrier stream, or other means by which a solid or viscous reagent can be immobilized. Flow of the carrier fluid over the solid reagent dissolves or suspends the reagent particles in the carrier stream.

Because the sample and carrier streams are layered rather than side by side, multiple reagent inlets can be positioned side by side in parallel to allow simultaneous detection of multiple analytes. A layered flow of sample and carrier streams is established and reagents are introduced into the carrier stream using parallel inlets which are narrow compared to the width of the carrier stream. The reagent inlets are spaced sufficiently far apart that there need be no undesired inter diffusion between the reagents. Optical measurement of analyte concentrations can be made by multiwave two-dimensional imaging. Multiple analytes can be detected simultaneously using equipment as simple as a camera. Electrochemical detection can utilize a plurality of electrodes placed in the flow channel.

A second reagent inlet can be positioned downstream of and in series with the first reagent inlet for sequential addition of reagents. The first and second inlets can be used, for example, to admit first and second antibodies for sandwich assay of an antigen. In another example, the first inlet admits a reagent which reacts with the analyte to form a product, and the second inlet admits an indicator for the product. For example, to detect glucose the first reagent can be glucose oxidase and the second a pH sensor.

The preferred embodiments of this invention utilize liquid streams, although the methods and devices are also suitable for use with gaseous streams.

The channel cell system of this invention can be used with external detecting means for detecting changes in reagent particles as a result of contact with analyte particles. Detection is done by optical, electrical, chemical, electrochemical, radioactive or calorimetric analysis, or any other technique in the analytical art. More than one detection technique can be used in the same system. The preferred embodiments use optical analysis or a combination of electrochemical and optical analysis. In optical detection, the product stream can be analyzed by luminescence, fluorescence or absorbance. The reagent can be a chemical indicator which changes color or other properties when exposed to the analyte. The reagent can comprise substrate particles such as polymers or beads having a reagent particle immobilized thereon, as described in U.S. patent application Ser. No. 08/621,170, filed Mar. 20, 1996, now U.S. Pat. No. 5,747,349, which is incorporated by reference herein in its entirety.

The term "detection" as used herein means determination that a particular substance is present. Typically, the concentration of a particular substance is also determined. The concentration of the analyte particles in the sample stream is determined by detecting the position within the laminar flow channel at which a detectable change in the reagent particles is caused. Generally there is not a distinct boundary in the channel at which a detectable change occurs, but rather a gradient in the detected property. The detection gradient can be used to provide information about flow speed and/or sample concentration.

The detection gradient for a given analyte stays the same over time as long as the flow speed is constant and the sample unchanged. The gradient can be varied by varying flow rate, sample concentration, and/or reagent concentration so as to optimize the signal for detection. For example, the system can be adjusted so that the gradient falls in the central portion of the device. If the flow rates and reagent concentration are known, the analyte concentration can be determined from the gradient.

The sample stream may be any stream containing an analyte and, optionally, also containing less diffusive particles, for example blood or other body fluids, contaminated drinking water, contaminated organic solvents, biotechnological process samples, e.g. fermentation broths, and the like. The analyte can be any particle in the sample stream which is capable of diffusing into the carrier stream in the device. The term "small particle" is used herein for any particle sufficiently diffusive to diffuse between streams within the length of the flow channel. Examples of analyte particles are hydrogen, calcium, sodium and other ions, dissolved oxygen, proteins such as albumin, organic molecules such as alcohols and sugars, drugs such as salicylic acid, halothane and narcotics, pesticides, heavy metals, organic and inorganic polymers, viruses, small cells and other particles. Preferably the analyte particles are no larger than about 3 micrometers, more preferably no larger than about 0.5 micrometers, or are no larger than about 1,000,000 MW, and more preferably no larger than about 50,000 MW.

The carrier can be any fluid capable of accepting particles diffusing from the sample stream and reagent inlet. Preferred carrier streams comprise water and isotonic solutions such as salt water, or organic solvents like acetone, isopropyl alcohol, ethanol, or any other liquid convenient which does not interfere with the effect of the analyte on the reagent, or interfere with the detection means.

The channel cell is generally formed by two plates with abutting surfaces. The channels may be formed in both plates, or one plate can contain the channels and the other can be a flat cover plate. Substrate plate as used herein refers to the piece of material in which the channel system of this invention is formed, e.g., silicon wafer and plastics. The channel cell may be fabricated by microfabrication methods known to the art, e.g. by forming channels in a silicon microchip and placing a glass cover over the surface, or precision injection molding plastic.

For optical detection, such as absorption, luminescence or fluorescence detection, at least a portion of the channel in the analyte detection area is transparent. Optionally other parts of the channel cell system are also transparent. Analyte detection area as used herein refers to that portion of a flow channel where a detectable change in the analyte or reagent particles is measured.

For electrochemical detection, one or more electrodes is positioned in the detection area.

For turgid sample fluids, the electrodes are preferably placed on the carrier fluid side to prevent fouling of the electrodes. For multiple analytes, multiple electrodes are placed in parallel. To measure the detection gradient for each analyte, multiple electrodes can be positioned in series. The position of the electrodes can be used to distinguish between analytes having similar redox potentials but different diffusion coefficients. The electrodes can be deposited on the channel surface, on either or both plates.

The method of this invention is designed to be carried out such that all flow is laminar. In general, this is achieved in a device comprising microchannels of a size such that the Reynolds number for flow within the channel is below about 1, preferably below about 0.1. Reynolds number is the ratio of inertia to viscosity. Low Reynolds number means that inertia is essentially negligible, turbulence is essentially negligible, and the flow of the two adjacent streams is laminar, i.e. the streams do not mix except for the diffusion of particles as described above. Flow can be laminar with Reynolds number greater than 1. However, such systems are prone to developing turbulence when the flow pattern is disturbed, e.g., when the flow speed of a stream is changed, or when the viscosity of a stream is changed.

The laminar flow channel is long enough to permit small analyte particles to diffuse from the sample stream and have a detectable effect on reagent particles, preferably at least about 2 mm long. The diffusion time required depends on the diffusion coefficient of the analyte particles. The reaction time required depends on the reaction rate. Some reactions, such as ion reactions, are completed within microseconds. Some reactions, such as competitive immunoassays that involve unloading a bound antigen, require a few minutes.

To allow greater time for reaction between the analyte particles and the reagent particles, the length of the product stream channel can be increased. The length of the flow channel depends on its geometry. The flow channel can be straight or convoluted in any of a number of ways. In one embodiment, the flow channel can include a series of turns, making a stairstep or square wave geometry. Convoluted channels provide longer distances for diffusion to occur without increasing the size of the substrate plate in which the channel is formed, thereby allowing for measurement of analytes with larger diffusion coefficients. The diffusion coefficient of the analyte, which is usually inversely proportional to the size of the analyte, affects the desired flow channel length. For a given flow speed, particles with smaller diffusion coefficients require a longer flow channel to have time to diffuse into the carrier stream. In preferred embodiments of this invention the channel length of a straight flow channel is between about 5 mm and about 50 mm. In embodiments of this invention wherein the flow channel is convoluted, the length of the flow channel is defined or limited only by the size of the microchip or other material into which the channel is etched or otherwise formed.

As an alternative to increasing channel length to allow more time for diffusion to occur, the flow rate can be decreased. However, several factors limit the minimum flow rate and therefore make a longer flow channel desirable in some cases. First, the flow rate is typically achieved by a pumping means and some types of pumps cannot produce as low a pressure and flow rate as may be desired to allow enough time for diffusion of particles with small diffusion coefficients. Second, if the flow rate is slow enough and some particles are of significantly different density from the surrounding fluid streams, particles denser than the surrounding fluid streams may sink to the bottom of the flow channel and particles less dense than the surrounding fluid streams may float to the top of the flow channel. It is preferable that the flow rate be fast enough that hydrodynamic forces substantially prevent particles from sinking to the bottom, floating to the top, or sticking to the walls of the flow channel. The flow rate of the input streams is preferably between about 5 micrometers/second and about 5000 micrometers/second, more preferably about 25 micrometers/second. For systems wherein sedimentation is not a problem, the flow can be stopped to allow greater time for diffusion and reaction and then resumed. Preferably the flow rate for both the sample and carrier streams is the same.

The channel depth (diffusion direction) is preferably between about 5 and 500 $\mu$m. The channel depth is small enough to allow laminar flow of two layered streams, preferably no greater than about 200 micrometers and more preferably between about 50 micrometers and about 100 micrometers. However, the channel can be made as shallow as possible while avoiding clogging the channel with the particles being used. Decreasing the depth of the channel makes diffusion of analytes into the carrier stream occur more rapidly, and thus detection can be done more rapidly.

The channel width can be as large as desired, since the laminar flow is relatively insensitive to width. The preferred width depends primarily on the number of parallel reagent inlets. Typically the width is between 0.1 and 1 cm. A 1 cm wide channel can accommodate 10 parallel reagent inlets, for 10 analytes.

For detecting analytes optically in turbid and strongly colored solutions such as blood, the sample fluid is preferably filtered before measurement. The filter can be any filter known in the art. It can also be a diffusion based microfilter device comprising microchannels in the shape of an "H", as disclosed in U.S. patent application Ser. No. 08/663,916, filed Jun. 14, 1996, U.S. Pat. No. 5,932,100, which is incorporated by reference in its entirety herein. In the microfilter, the unfiltered-sample stream, which is a mixture of particles suspended in a fluid, and an extraction stream join in the central channel (the crossbar of the "H") and flow together in the central channel. Due to the small size of the channels, the flow is laminar and the streams do not mix. The residual-sample stream and the extraction stream split at the other end of the channel. While the streams are in laminar flow contact in the central channel, particles having a greater diffusion coefficient (smaller particles) have time to diffuse into the extraction stream, while the larger particles (e.g. blood cells) remain in the sample stream. Particles in the exiting extraction stream (now called the filtered sample stream) may be analyzed without interference from the larger particles. In the present invention the microfilter can be formed in the plane perpendicular to the wafer surface rather than in the plane of the surface.

Information useful for determining the concentration of the analyte particles in the sample stream can be obtained by providing means for conducting specimen streams from the carrier stream at successive intervals along the length of the laminar flow channel, as described in U.S. patent applications Ser. No. 08/829,679, filed Mar. 31, 1997, now U.S. Pat. No. 5,972,710, and 08/625,808, filed Mar. 29, 1996, U.S. Pat. No. 5,716,852.

Dual detection embodiments of the device of the present invention which allow for detection of both undissolved and dissolved analytes are also provided. Detection of both undissolved and dissolved analytes can be achieved in one dual detection device with branching flow channels in fluid connection with the flow channel of the diffusion based sensor. Undissolved particles are preferably detected with a flow cytometer. The fluid streams can flow first through a diffusion based sensor flow channel for detection of dissolved particles, and then through a branching channel to a flow cytometer for detection of undissolved particles. Alternatively, the fluid stream can flow first through a flow cytometer and then through a diffusion based sensor flow channel.

One embodiment of the flow cytometer uses a v-groove flow channel. The v-groove channel is described in detail in U.S. patent application Ser. No. 08/534,515, filed Sep. 27, 1995, U.S. Pat. No. 5,726,751, which is incorporated by reference herein in its entirety. The cross-section of such a channel is like a letter V, and thus is referred to as a v-groove channel. The v-groove preferably has a width small enough to force the particles into single file, but large enough to pass the largest particles without clogging. An optical head comprising a laser and small and large angle photodetectors adapted for use with a v-groove flow channel can be employed.

An alternative means of achieving single file particle flow through a flow channel is the sheath flow module disclosed in U.S. patent application Ser. No. 08/823,747, filed Mar. 26, 1997 and incorporated in its entirety by reference herein. The sheath flow module includes sheath fluid inlets before and after, and wider than, a sample inlet.

Inlets, which comprise the inlet channels, can also include other means such as tubes, syringes, pumps, and the like which provide means for injecting fluid into the device. Outlets can include collection ports, and/or means for removing fluid from the outlet, including receptacles for the fluid, means for inducing flow, such as by capillary action, pressure, gravity, and other means known to the art. Such receptacles may be coupled to an analytical or detection device.

The method can be conducted by a continuous flow-through of sample and carrier streams. The steady-state nature of this method makes longer signal integration times possible.

Additionally, a method is provided for determining kinetic rate constants as a function of the detection gradient. Generally, kinetic measurements are made by plotting a physical property versus time, i.e., time of reaction. The method provided herein for making kinetic measurements as a function of distance traveled by the sample and reagent, rather than time, is advantageous in that it allows for integrating the data from detection over time, thereby increasing the accuracy of the data collected.

BRIEF DESCRIPTION OF THE DRAWINGS

FIG. 1, comprising

FIG. 2, comprising

DETAILED DESCRIPTION OF THE INVENTION

This invention relates to the following co-pending Patent Applications, all of which are incorporated by reference in their entirety: U.S. Ser. No. 08/625,808, "Microfabricated Diffusion-Based Chemical Sensor," filed Mar. 29, 1996, now U.S. Pat. No. 5,716,852; U.S. Ser. No. 08/829,679, "Microfabricated Diffusion-Based Chemical Sensor," filed Mar. 31, 1997, now U.S. Pat. No. 5,972,710 U.S. patent application Ser. No. 08/900,926 "Simultaneous Analyte Determination and Reference Balancing in Reference T-Sensor Devices," filed Jul. 25, 1997, now U.S. Pat. No. 5,948,684 U.S. Ser. No. 08/621,170 "Fluorescent Reporter Beads for Fluid Analysis," filed Mar. 20, 1996, U.S. Pat. No. 747,349; U.S. Ser. No. 08/663,916, "Microfabricated Differential Extraction Device and Method," filed Jun. 14, 1996, U.S. Pat. No. 5,932,100; U.S. Ser. No. 08/534,515, "Silicon Microchannel Optical Flow Cytometer," filed Sep. 27, 1995, U.S. Pat. No. 5,726,751; PCT Publication No. WO 97/12223, "Silicon Microchannel Optical Flow Cytometer," filed Sep. 27, 1996; U.S. Ser. No. 08/823,747, "Device and Method For 3-Dimensional Alignment of Particles in Microfabricated Flow Channels," filed Mar. 26,1997; U.S. Ser. No. 08/876,038, "Adsorption-Enhanced Differential Extraction Device," filed Jun. 13, 1997, now U.S. Pat. No. 5,971,158 U.S. Ser. No. 60/049,533, "Method For Determining Concentration of a Laminar Sample Stream," filed Jun. 13, 1997; U.S. Ser. No. 08/938,585, "Simultaneous Particle Separation and Chemical Reaction," filed concurrently herewith; U.S. Ser. No. 08/938,584, "Device for Rapidly Joining and Splitting Fluid Layers," filed concurrently herewith.

Figure 1A:
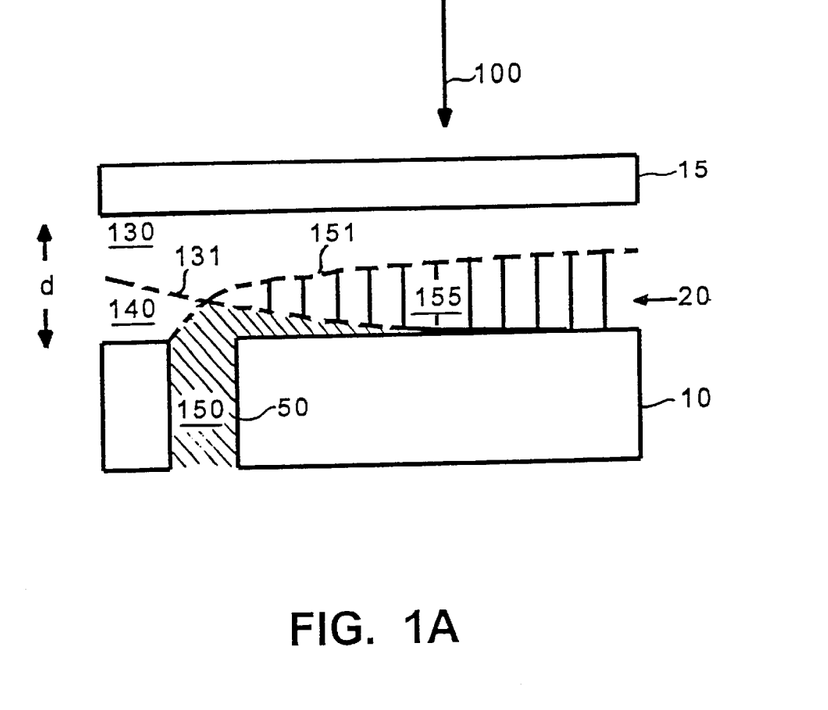
FIGS. 1a–b, is (a) a cross section and (b) a plan view of a reagent inlet and of the change in reagent particles on interaction with analyte particles.
Figure 1B:
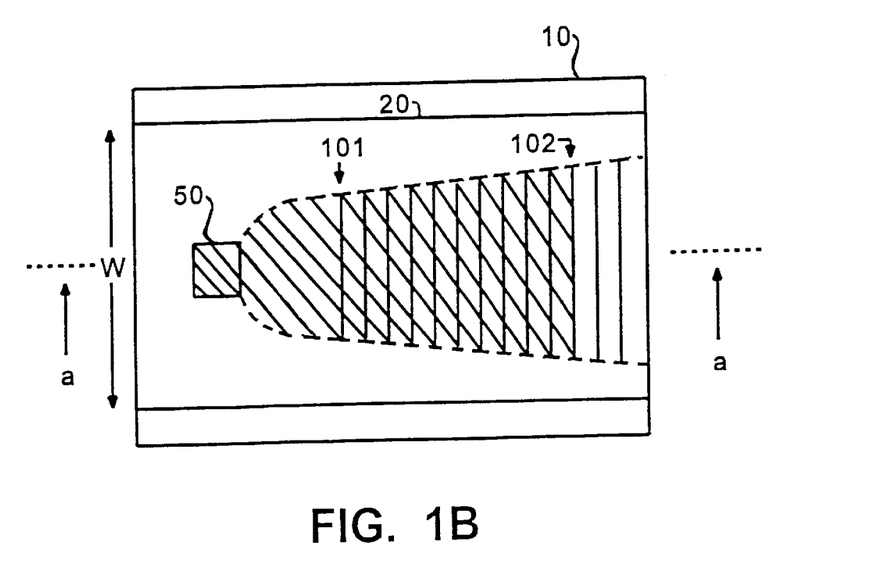

The operation of the diffusion based sensor of this invention is shown in FIG. 1 in (a) cross section and (b) plan view. Flow channels and inlets and outlets are formed in substrate plate 10, covered by transparent cover plate 15. Laminar flows of sample stream 130 and carrier stream 140 are established in channel 20. Due to the low Reynolds number in the small flow channel, no turbulence-induced mixing occurs and the two streams flow parallel to each other without mixing. However, because of the short distances involved, diffusion does act perpendicular to the flow direction, so sample components (analyte particles) diffuse from the sample stream to the carrier stream. The smaller sample components diffuse more rapidly and equilibrate close to the reagent inlet, whereas larger components equilibrate farther up in flow channel 20. The diffusion of analyte particles is indicated by dashed line 131.

Reagent 150 enters the flow channel through fluid inlet 50, and reagent particles diffuse into the carrier stream, as indicated by dashed line 151. The interaction of the analyte particles with the reagent particles changes a detectable property of the reagent particles. In this example, the reagent turns from green before reaction (150) to red after reaction (155).

The interaction is viewed from above, as indicated by detection axis 100, and as shown in FIG. 1b. At the inlet the reagent is green. As analyte particles contact reagent particles, when viewed from above the cell the fluid in the channel begins to appear somewhat red in addition to green. The change in color becomes observable at the start 101 of the detection gradient. Moving downstream, the green fades out and the red increases in intensity until only red is observed at the end 102 of the detection gradient. Although this is a flow system, the physical location of the detection gradient in the flow channel stays the same over time as long as the flows are constant and the sample unchanged. The presence of analyte is detected by a change in a property, in this case absorbance. The concentration of the analyte can be determined from the distance it takes to change the property, and in particular from the detection gradient.

In the illustrated example, the absorbance of the reagent particle changes and the sensor is monitored in transmission. Plates 10 and 15 are made of an optically transparent material such as glass or plastic. The optical apparatus can be very simple. The sensor can be illuminated on one side with a light source such as a light bulb and diffuser, and the absorbance can be detected on the other side with a camera or even a human eye. Alternatively the fluorescence of analyte particles can change in response to the analyte, in which case the fluorescence can be monitored.

In another embodiment the reaction of the analyte and reagent makes a luminescent product. For reflection measurements plate 10 need not be transparent, and is preferably made of a reflective material such as silicon.

Although the sensor is illustrated with optical detection, other detection means can be employed. In particular, the sensor is suited to electrochemical detection.

Figure 2A:
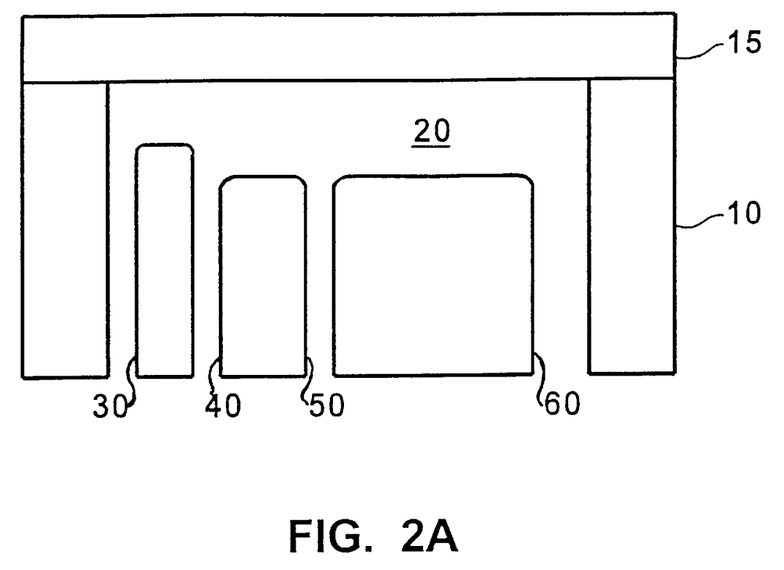
FIGS. 2a–b, is (a) a cross section and (b) a plan view of a diffusion based sensor having three reagent inlets in parallel.
Figure 2B:
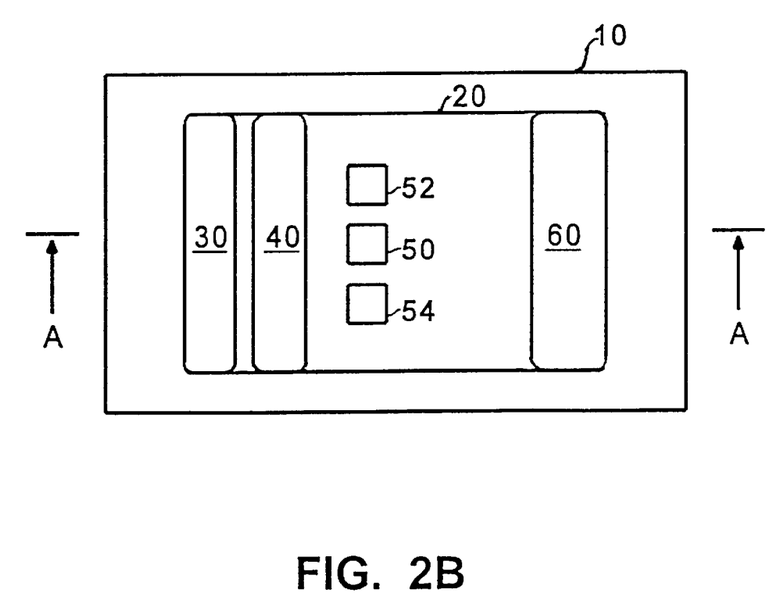

The structure of an embodiment of the sensor is shown in FIG. 2 in (a) cross section and (b) plan view. Sample inlet 30 passes through substrate plate 10 into channel 20. Carrier inlet 40 joins the bottom of channel 20. The terms bottom and top as used herein refer to the substrate plate and the cover plate sides of the channel, respectively, although the cell need not necessarily be oriented in use with the substrate plate on the bottom. In fact, because particles such as blood cells sediment in fluids such as plasma, it is preferred that the sensor be oriented with the sample stream below the carrier stream if the sample stream is turbid. If the cell is fabricated in a way which does not utilize substrate and cover plates, the top is the side with the sample fluid and the bottom is the side with the carrier fluid. In a preferred embodiment the depth of the channel increases at the carrier inlet to accommodate the carrier stream. In the illustrated embodiment a plurality of reagent inlets, 50, 52 and 54, positioned in parallel, join the flow channel at the bottom, between carrier inlet 40 and outlet 60. Parallel inlets need not be lined up as illustrated, but are laterally positioned in different parts of the stream.

Preferably the depth does not increase at the reagent inlets. The flowing layers are not perturbed because the reagent inlets are narrower than the channel and because the reagent volume is small relative to the sample and carrier stream volumes. In this embodiment, all fluid streams exit through outlet 60. Alternatively, specimen channels can branch from the side or bottom of the channel before the outlet.

Each reagent inlet can be used for a different reagent, and multiple analytes can be simultaneously detected. In one embodiment, the spacing of the different reagent inlets is far enough apart so that there is no significant mixing or interaction between reagents. Alternatively, to avoid crosstalk partitions can be placed between separate flow streams. In a second embodiment, the reagent inlets are spaced so that the reagent plumes overlap, and the interaction region can be monitored.

Figure 3:
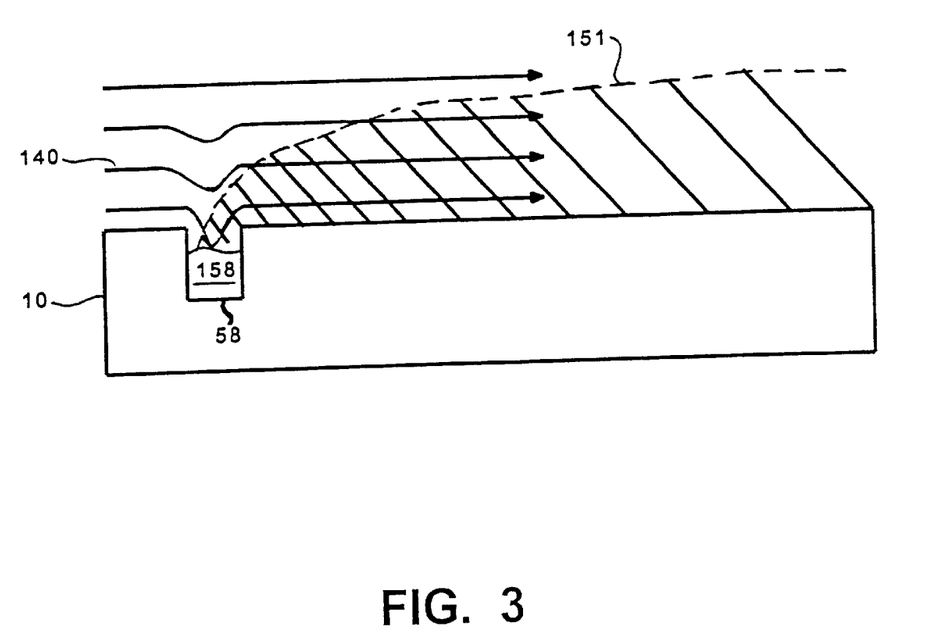
FIG. 3 is a cross section of a solid reagent inlet with reagent diffusing into a carrier fluid.

The sensor has been illustrated with fluid reagent inlet 50. The reagent particles can be in solution or can be immobilized on a bead carried by a fluid. In lieu of a fluid inlet, a solid reagent inlet can be employed, as illustrated in FIG. 3. Plate 10 has cavity 58 which can be filled with a solid pellet of reagent 158. For the case of multiple reagents there is a series of cavities. The term pellet is used herein for a solid or viscous mass of reagent which can be immobilized on the sensor plate. It can be recessed in a cavity, as shown, or can sit on the surface of the plate. Carrier stream 140 flows over the reagent pellet and carries the dissolved or suspended reagent downstream, as shown by dashed line 151.

The reagent pellet is preferably soluble in the carrier fluid. The pellet can utilize a soluble reagent carrier, for example a sugar such as trehalose. The reagent pellet is placed into the sensor before use. Preformed pieces of dry reagent can be inserted or, more simply, a solution of the reagent can be injected into the cavity followed by immobilizing the reagent by a process such as drying or gelation. After insertion of the reagent pellet, the sensor is assembled for use. This embodiment, with solid reagent pellets, is particularly suited for disposable use.

Because the flow channel operates in low Reynolds number conditions, the flow of the carrier across the solid pellet maintains a smooth flow. The flow velocity immediately over the pellet varies as the pellet shrinks, and, for a cavity placed pellet, the cavity deepens. The dissolution rate of the analyte varies over time as the pellet shrinks. Reproducibility can be improved by making the measurements at a specific point during the dissolution process. The measurement point can be determined, in one embodiment, by the rate of dissolution of a reference substance. An adjacent cavity contains a fluorescent or otherwise easily traceable marker immobilized in a pellet with similar dispersal characteristics to the reagent pellet. Alternatively, the system can be calibrated with a calibrant solution before and/or after sample measurements. In another embodiment, the rate of dissolution is made relatively constant by modifying the shape of the cavity or by layering different reagent/reagent-carrier mixtures.

Reporter beads as the reagent can be introduced through a liquid or solid reagent inlet. For cases when the reagent is immobilized on a bead, the reagent does not appreciably diffuse into the carrier stream, and the analyte must diffuse through the carrier stream to the reagent. Reporter beads can be used to measure pH, oxygen saturation, ion content, alcohols, pesticides, organic salts such as lactate, sugars such as glucose, heavy metals, and drugs such as salicylic acid, halothane and narcotics. Each reporter bead comprises a bead having a plurality of at least one type of fluorescent reporter molecules immobilized thereon. A fluorescent or absorption property of the reporter bead is sensitive to a corresponding analyte. Reporter beads can be added at the reagent inlet and the analyte concentration can be determined by observing the sensor flow channel from above or by removing beads and analyte through a specimen channel and measuring individual beads, for example in a flow cytometer. When removed in a specimen channel, the use of reporter beads allows for a plurality of analytes to be measured simultaneously through a single reagent inlet because the beads can be tagged with different reporter molecules.

Magnetic beads can be used as the reporter beads. In this embodiment, the beads are pulled into the sample stream by a magnetic field. They can be immobilized to allow longer contact time with the analyte. Optionally, they can be pulled back into the carrier stream, for example for contact with a second analyte.

When the sample is a turbid sample, such as blood, it is useful to filter the sample before measurement, especially for optical measurement. While any filter known in the art can be employed, a preferred filter is a diffusion based microfilter, as described in U.S. Patent application Ser. No. 08/663,916, U.S. Pat. No. 5,932,100. The filter can lie in the plane of the substrate or a plane perpendicular to the substrate. The perpendicular filter is shown in combination with a sensor in FIG. 4. Unfiltered-sample fluid 180 enters through inlet 80 and extraction fluid 170 enters through inlet 70. The two fluids flow in adjacent laminar streams in the filter's laminar flow channel, and analyte particles from the sample fluid diffuse into the extraction stream. The remaining turbid material 190, such as cells, termed herein the residual sample, is discharged through outlet 90. Because particles such as blood cells sediment in fluids such as plasma, it is preferred that the filter be oriented with the turbid sample stream below the extraction stream. The extraction stream of the filter is the sample stream for the sensor, and enters through sample inlet 30. In the sensor, carrier fluid 140 joins the sample stream through inlet 40.

Figure 4:
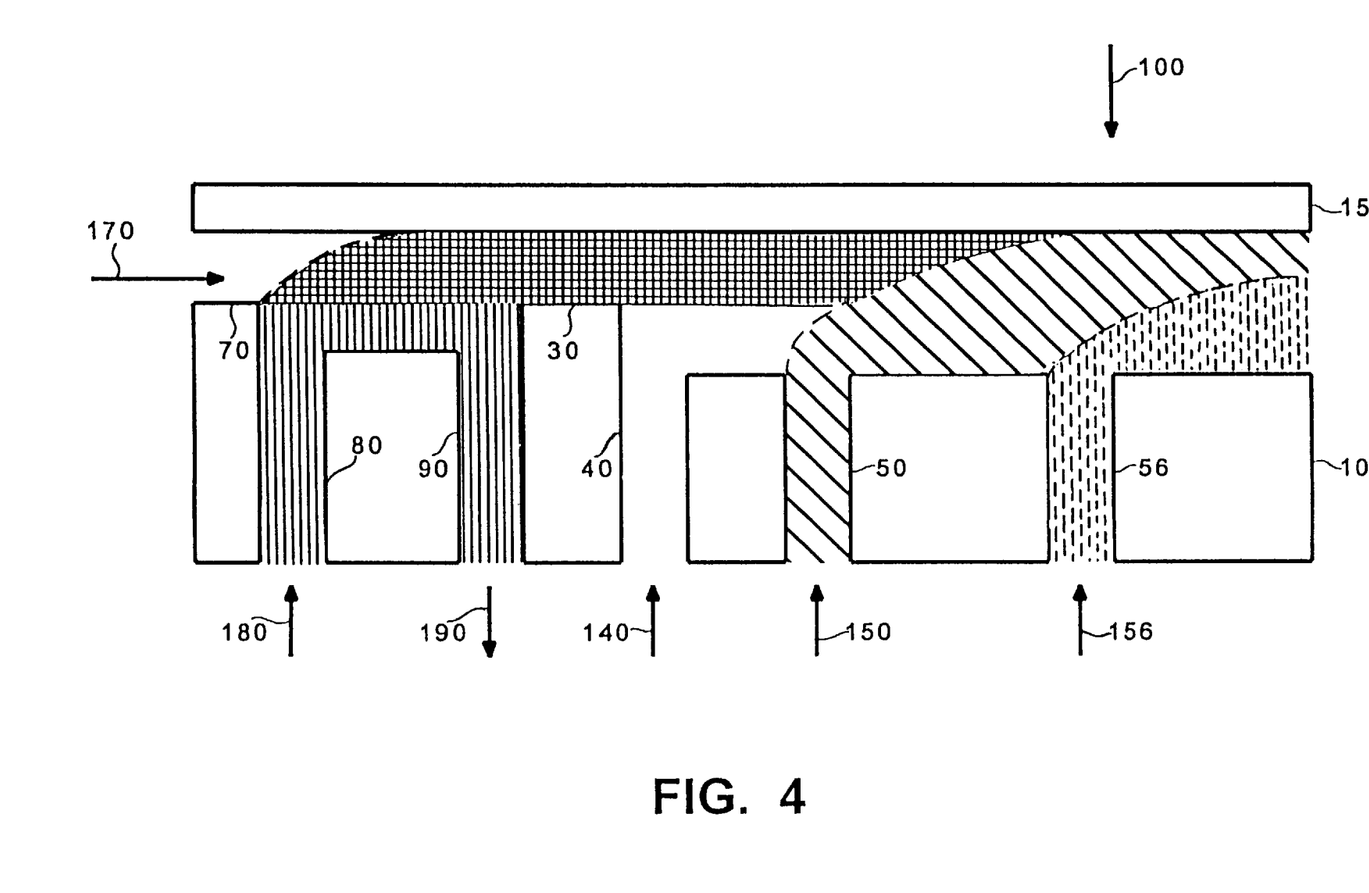
FIG. 4 is a cross section of a sensor having two reagent inlets in series and having a preceding diffusion based microfilter.

Fluid reagent 150 enters through inlet 50, and reagent particles diffuse through the carrier stream. Changes in optical properties on interaction with the analyte are not illustrated in this figure.

A second reagent 156 can enter downstream of the first reagent through port 56 positioned in series with the first reagent inlet. Electrodes 51 and 57 useful for electrochemical detection maybe placed between the reagent inlets 50 and 56 and the outlet. Sequential addition of reagents is used, for example, in sandwich assays. For example, when the analyte is an antigen the first reagent can be a bead with a selective antibody and the second reagent can be a secondary antibody with an attached flourophor. In another example of an embodiment using multiple reagents in series, the sample stream is blood, the first reagent is glucose oxidase, and the second reagent contains a pH sensitive dye. As glucose particles from the blood diffuse into the carrier stream they are changed to gluconic acid which is detected by the pH-sensitive dye.

Means for applying pressure to the flow of the feed fluids through the device can also be provided. Such means can be provided at the feed inlets and/or the outlet (e.g. as vacuum exerted by chemical or mechanical means). Means for applying such pressure are known to the art, and include the use of a column of water or other means of applying water pressure, electroendoosmotic forces, optical forces, gravitational forces, and surface tension forces. Rather than a pressure source, a flow source can be used at the inlets, for example a syringe.

The channel cells of this invention and the channels therein can be sized as determined by the size of the particles desired to be detected. As is known in the art, the diffusion coefficient for the analyte particles is generally inversely related to the size of the particle. Once the diffusion coefficient for the particles desired to be detected is known, the contact time of the two streams, size of the central channel, relative volumes of the streams, pressure and velocities of the streams can be adjusted to achieve the desired diffusion pattern.

Fluid dynamic behavior is directly related to the Reynolds number of the flow. As the Reynolds number is reduced, flow patterns depend more on viscous effects and less on inertial effects. Below a certain Reynolds number, e.g., 0.1, inertial effects can essentially be ignored. The microfluidic devices of this invention do not require inertial effects to perform their tasks, and therefore have no inherent limit on their miniaturization due to Reynolds number effects. The devices of this invention require laminar, non-turbulent flow and are designed according to the foregoing principles to produce flow having low Reynolds numbers, i.e. Reynolds numbers below about 1.

The devices of the preferred embodiment of this invention are capable of analyzing a sample of a size between about 0.01 microliters and about 20 microliters within a few seconds, e.g. within about three seconds. For fluid reagent inlets, the devices may be reused. Clogging is minimized and reversible.

By adjusting the configuration of the channels in accordance with the principles discussed above to provide an appropriate channel length, flow velocity and contact time between the sample stream and the carrier stream, the size of the particles remaining in the sample stream and diffusing into the carrier stream can be controlled.

For some analytes with relatively small diffusion coefficients, a straight channel does not provide a long enough flow channel for diffusion to occur adequately. Detection of analytes with relatively small diffusion coefficients, e.g. relatively large analytes or non-spherical analytes, preferably employs a convoluted flow channel.

The channel cell system of this invention can be used to measure concentration of an analyte as a function of distance (from the reagent inlet) rather than time. An increment of distance is proportional to an increment of time. With laminar flow and a known flow speed, an increment of distance can be converted to an increment of time. The rate of, or rate constant for, a reaction can be determined using the diffusion based sensor of this invention. If the analyte concentration is known, the rate of reaction with the reagent can be obtained from the detection gradient. A rate constant for a reaction can be determined with only one measurement.

This invention has been described in a few preferred embodiments. Many variations falling within the spirit and scope of the invention will be readily apparent to those skilled in the art. Application of the channel system of this invention for use as a sensor has been described. It can also be used to synthesize multiple products as opposed to sensing multiple analytes. In the reactor embodiment, the "sample" stream contains a first reagent, which reacts with a reagent from the reagent inlet to form a product. In this embodiment the product is collected rather than detected. Since the structure is the same, the device is herein termed a sensor, though it may also be used as a reactor.

A few specific chemical reactions have been recited; any reaction or interaction which produces a detectable change in either the reagent or analyte can be used. A few detection means have been described; other analytical means can be employed. The sensor can be coupled with pretreatment and post treatment apparatuses, such as fillers, separators, reactors and detectors. The device can include additional inlets and outlets. The scope is limited only by the following claims and their equivalents.

I claim:

1. A method of detecting the presence of first analyte particles in a sample stream, comprising the steps of:
   conducting said sample stream into a laminar flow channel;
   conducting a carrier stream into said laminar flow channel such that said sample stream and said carrier stream flow in layered laminar streams;
   conducting a first reagent, containing first reagent particles, into said laminar flow channel such that said reagent comes in contact with said carrier stream;
   allowing said first analyte particles to diffuse into said carrier stream; and
   detecting the reaction of said first analyte particles with said first reagent particles.

2. The method of claim 1 further comprising the step of conducting a second reagent, containing second reagent particles, into said channel.

3. The method of claim 2 wherein said first and second reagents are conducted into said channel in parallel.

4. The method of claim 2 wherein said first and second reagents are conducted into said channel in series.

5. The method of claim 1 wherein said channel has a Reynolds number R<1.

6. The method of claim 5 wherein said channel has a Reynolds number R<0.1.

7. The method of claim 1 wherein said first reagent is a fluid reagent.

8. The method of claim 7 wherein said first reagent particles are immobilized on beads, said beads carried within said fluid reagent.

9. The method of claim 8 wherein said beads further comprise a second reagent immobilized thereon.

10. The method of claim 1 wherein said first reagent is a solid reagent.

11. The method of claim 10 wherein said solid reagent comprises a reagent pellet recessed in a cavity in said channel.

12. The method of claim 10 wherein said pellet comprises reagent particles in a soluble reagent carrier.

13. The method of claim 1 wherein said sample stream has a volume <20 microliter.

14. The method of claim 1 wherein said sample stream also contains larger particles, further including the step of filtering said sample stream before conducting said sample stream into said flow channel.

15. The method of claim 14 wherein said step of filtering comprises the step of separating by diffusion said larger particles from said first analyte particles.

16. The method of claim 15 wherein said step of filtering further comprises the steps of:

establishing a laminar flow stream comprising an extraction stream adjacent to an unfiltered-sample stream;

wherein said step of separating comprises diffusion of said first analyte particles, but not said larger particles, from said unfiltered-sample stream to said extraction stream, whereby said unfiltered-sample stream becomes a residual-sample stream and said extraction stream becomes said sample stream; and further comprising the step of separating said residual-sample stream from said sample stream.

17. The method of claim 1 wherein said reaction causes a change in an optical property of said first analyte or first reagent particles and wherein said step of detecting comprises an optical measurement.

18. The method of claim 17 wherein said step of detecting comprises an absorbance measurement.

19. The method of claim 18 wherein said absorbance measurement is carried out continuously along a portion of said laminar flow channel.

20. The method of claim 19 wherein said absorbance measurement comprises illuminating said channel with a light source and photographing said channel with a camera.

21. The method of claim 20 wherein said camera is a digital camera.

22. The method of claim 17 wherein said step of detecting comprises a fluorescence measurement.

23. The method of claim 17 wherein said step of detecting comprises a luminescence measurement.

24. The method of claim 1 wherein said reaction causes a change in an electrical property of said first analyte or first reagent particles and wherein said step of detecting comprises an electrical measurement.

25. The method of claim 24 wherein said electrical measurement is performed at a plurality of sequential positions in said channel.

26. The method of claim 1 further comprising a calibration performed before or after sample measurement, said calibration comprising the steps of:

conducting a calibration stream into said laminar flow channel, said calibration stream containing a known concentration of first analyte particles;

conducting a carrier stream into said laminar flow channel such that said calibration stream and said carrier stream flow in layered laminar streams;

conducting a first reagent, containing first reagent particles, into said laminar flow channel such that said reagent comes in contact with said carrier stream;

allowing said first analyte particles to diffuse into said carrier stream;

detecting the reaction of said first analyte particles with said first reagent particles; and calibrating the sensitivity of the detection of said first analyte.

* * * * *